United States Patent [19]

LeRoy

[11] Patent Number: 5,276,056
[45] Date of Patent: Jan. 4, 1994

[54] METHOD AND COMPOSITION FOR TREATING EQUINE ANHIDROSIS

[76] Inventor: Raymond F. LeRoy, 13150 North 22nd Ave., Phoenix, Ariz. 85029

[21] Appl. No.: 874,055

[22] Filed: Apr. 24, 1992

[51] Int. Cl.$^5$ .................. A61K 31/195; A61K 35/78; A61K 33/26; A61K 31/685

[52] U.S. Cl. ................................ 514/567; 424/195.1; 424/646; 514/78

[58] Field of Search ............... 424/195.1, 646; 514/78, 514/567

[56] References Cited

U.S. PATENT DOCUMENTS

| | | | |
|---|---|---|---|
| 4,386,062 | 5/1983 | Beadle | 424/9 |
| 4,737,489 | 4/1988 | Wurtman | 514/76 |
| 4,767,704 | 8/1988 | Cleveland et al. | 435/240.31 |

OTHER PUBLICATIONS

Ralston et al., "Treat of Anhidrotic Horses with L. Tyrosine and Cobalt", Aug. 1990.
Braveman et al., *The Healing Nutrients Within*, Keats Publishing, Inc., copyright 1987, pp. 44–58 and 360–355.
Freestone, "Anhidrosis", *Current Therapy in Equine Medicine* 3, W. B. Saunders Company, 1992, pp. 703–704.
Snow et al., "Sweating and Anhidrosis", *Equine Sports Medicine*, vol. 5, No. 2, pp. 4, 5, 8, 1986.
Jenkinson et al., "Effects of Season and Lower Ambient Temperature on the Structure of the Sweat Glands in Anhidrotic Horses", *Equine Veterinary Journal*, (1989)21(1), pp. 59–65.
Larsen et al., *Human Metabolism*, "2, Main Map", Munksgaard, 1987.
*Biochemistry of the Essential Ultratrace Elements*, edited by Earl Frieden, Plenum Press, 1987, "Effect of Cobalt on Microorganisms", p. 143.
Warner, "Anhidrosis", *Current Therapy in Equine Medicine* 2, W. B. Saunders Company, 1987, pp. 187–188.
Arthur C. Guyton, M.D., *Medical Physiology*, "Circulation in the Skin: Physiologic Anatomy of the Cutaneous Circulation", W. B. Saunders, 1981, Chap. 29, pp. 352–356.
Arthur C. Guyton, M.D., *Medical Physiology*, W. B. Saunders, 1981, pp. 700–703 and 710–722.
Kerr, et al., "Composition of Sweat of the horse during prolonged epinephrine (adrenaline) infusion, heat exposure and exercise", *Am. J. Vet. Res.*, vol. 44, No. 8, Aug. 1983, pp. 1571–1577.
Masri, et al., "Andhidrosis", *Proc. 9th ACVIM Forum*, New Orleans, La. May 1991, pp. 405–407.
Correa, "Anhidrosis, Dry-Coat Syndrome in the Thoroughbred", *J.A.V.M.A.*, vol. 149, Dec. 1966, pp. 1556–1560.
Breen Vann, "Mare Management: The Thyroid Zone", *MHB*, Jun. 1989, pp. 2–8.
Romeiser, "The Take-Charge Thyroid", *EQUUS*, May, 1987, vol. 122, pp. 30–34.
Beech, "Evaluation of Thyroid, Adrenal and Pituitary Function", *The Veterinary Clinics of North America: Equine Practice*, vol. 3, No. 3, Dec. 1987, pp. 649–659.
Beadle et al., "Summertime plasma catecholamine concentrations in healthy and anhidrotic horses in Louisana", *Am. J. Vet. Res.*, vol. 43, No. 8, Aug. 1982, pp. 1446–1448.
Warner et al., "Equine anhidrosis: A survey of affected horses in Florida", *J.A.V.M.A.*, vol. 180, No. 6, Mar. 1982, pp. 627–629.
Arthur C. Guyton, *Textbook of Medical Physiology*, Sixth Edition, W. B. Saunders Company, 1981, pp. 886–898.
Ruch, et al., *Medical Physiology and Biophysics*, W. B. Saunders Company, 1960, pp. 999–1004.

*Primary Examiner*—Frederick E. Waddell
*Assistant Examiner*—Kevin E. Weddington
*Attorney, Agent, or Firm*—Cahill, Sutton & Thomas

[57] ABSTRACT

A method and composition for treating equine anhidrosis wherein a therapeutically effective amount of a composition of tyrosine, cobalt and iodine present as kelp is administered to the anhidrotic horse. The therapeutically effective amount of tyrosine is twice-daily dose of at least about 500 mg of tyrosine per 900 pounds of weight. The weight ratio of cobalt to tyrosine is in the range of about 0.0045–0.0055 and the weight ratio of kelp to tyrosine is in the range of about 0.00025–0.00030. Alternatively, lecithin can be added to the tyrosine to achieve a weight ratio of lecithin to tyrosine in the range of about 1.8–2.2.

17 Claims, No Drawings

METHOD AND COMPOSITION FOR TREATING EQUINE ANHIDROSIS

BACKGROUND OF THE INVENTION

The present invention relates to a method and composition for treating equine anhidrosis.

Equine anhidrosis, first reported in British thoroughbreds taken to tropical colonies early in this century, is also known as "nonsweating", "dry-coat syndrome", "blowing" or "puff disease" and is manifested by ineffective sweating in response to appropriate stimuli. Sweat evaporation is the primary cooling mechanism for horses when the ambient temperature exceeds the body temperature. Anhidrotic horses have compromised thermoregulatory function and are in great danger of hyperthermia. Normal equine rectal temperature is about 99.5–101.5° F.; if asked to perform at extremely high ambient temperatures, anhidrotic horses have been known to achieve rectal temperatures of 108° F. and may collapse and die if raced. Providing shade or decreasing activity gives these horses minimal relief.

Anhidrosis appears to be precipitated by heat stress in humid environments in horses that have perhaps never previously experienced such conditions. Owners and veterinarians report that over a period of weeks or months, affected horses first show either profuse or delayed sweating and then gradually lose the ability to sweat altogether. Surveys in Florida revealed that anhidrosis can affect horses of all ages, breeds, colors, and affects both native horses and animals undergoing acclimatization. Anhidrosis is equally prevalent in horses at all levels of exercise, from idle pleasure horses to racehorses.

Clinical features of anhidrotic horses and hypohidrotic (deficient perspiration) horses include rapid breathing (tachypnea), the most common sign reported, fatigue and loss of hair (alopecia), especially of the face. Some animals may have a decreased appetite or decreased water consumption and poor performance. Secondary signs include changes in the proteinaceous secretion along with sweat which leads to dull hair coat, hair loss, scales and pruritus. Residual sweat areas include the crest, the neck, brisket and perineum.

The pathogenesis of anhidrosis is unknown. The lack of sweating could be due to a number of possible flaws in a complex sequence of events from central nervous stimulation ("CNS") through sweat stimulation and secretion, to delivery of sweat to the skin surface. The inability to produce or deliver sweat in response to the stimulus of tropical heat may include: (1) changes in gland stimulation either due to not enough central stimulus from CNS or an interruption in the neural stimulation; or (2) changes in gland or duct function, due to impaired gland response or changes in the secretory process, which impairs delivery of sweat to the skin surface; or (3) metabolic derangement of fluid, electrolyte losses, or an endocrine disturbance.

Studies of the ultrastructure of the sweat gland of such horses indicate that the condition, induced by continuous climatic stress, results from a gradual failure of the mechanism of sweat production and culminates in secretory, or sweat gland, cell degeneration. As reported in Jenkinson et al., *Effects of Season and Lower Ambient Temperature on the Structure of the Sweat Glands in Anhidrotic Horses*, Equine Vet.J (1989), 21(1), 59–65, histologically, the secretory cells become thin, in some cases less than 50% of normal size. In addition, the thinner cells generally contain few cytoplasmic granules and often contain large lysosomes. Removal of the thermal stress under controlled and/or natural environment has resulted in restoration of the activity of sweat glands on most anhidrotic horses studied. Early studies of anhidrosis demonstrated that the secretory failure is associated with a progressive reduction in the response of the glands to catecholamines.

Sweat glands have been classically divided into the categories eccrine and apocrine, on the basis of mechanism of secretion. The sweat glands in the horse are associated with hair follicles and have been classified as apocrine. Involvement of myoepithelial contraction in extrusion of sweat seems to vary among species, but sweat secretion is known to be continuous in cattle and horses.

Both apocrine and eccrine sweat glands are under control of the sympathetic nervous system. Pharmacologic studies strongly suggest the apocrine glands are controlled by the adrenergic sympathetic system, characterized by nerve fiber endings which secrete the synaptic transmitter substance norepinephrine, also known as noradrenaline.

Experimentally, sustained generalized sweating can be stimulated in the horse by intravenous administration of epinephrine, or localized by intradermal injection of epinephrine. Equine sweat glands respond most vigorously to beta-2-adrenergic stimulation. Sweating can be suppressed by a beta-adrenergic blocker (propanolol) but not by a beta-1 antagonist (metoprolol) when followed by epinephrine administration, which supports this observation. Beta-2-agonist (terbutaline, clenbutarol, etc.) are safely used as sudorific agents to test anhidrosis.

Hormonal studies have not been conclusive. Base line levels of thyroid hormone appear to be normal in anhidrotic horses. Circulating epinephrine concentrations are higher in anhidrotic than in normal horses, which may be of major significance in determining the pathogenesis of the disease.

Anhidrotic horses have been treated in the past with sodium chloride, iodine, potassium, and thyroid hormones. However, such treatments have not generally proven useful. The present knowledge about equine anhidrosis thus fails to include an effective method and composition for treating the affliction.

SUMMARY OF THE INVENTION

Accordingly, it is an object of the present invention to provide an effective method for treating equine anhidrosis.

It is another object of the present invention to provide an effective composition for treating equine anhidrosis.

Briefly described, and in accordance with one embodiment, the invention can be summarized as a method for treating equine anhidrosis, comprising the step of administering to the anhidrotic horse a therapeutically effective amount of tyrosine. To facilitate the action of tyrosine, it is preferred to add cobalt and kelp in amounts sufficient that the weight ratio of cobalt to tyrosine is in the range of about 0.0045–0.0055 and the weight ratio of kelp to tyrosine is in the range of about 0.00025–0.00030.

In a second embodiment, lecithin is added to the tyrosine in an amount sufficient to achieve a weight ratio of lecithin to tyrosine in the range of about 1.8 to 2.2. As with the first embodiment, it is preferred to add cobalt and kelp to the tyrosine and lecithin in amounts sufficient that the weight ratio of cobalt to tyrosine is in the range of about 0.008–0.0012 and the weight ratio of kelp to tyrosine is in the range of about 0.00050–0.00060.

DESCRIPTION OF THE PREFERRED EMBODIMENTS

The present invention is a method and composition for treating equine anhidrosis. In a first embodiment, the method comprises the step of administering to an anhidrotic horse weighing approximately 900–1000 pounds a twice-daily dose of at least 500 mg of the amino acid tyrosine (also known as "L-tyrosine"); such an amount of tyrosine is therapeutically effective in treating anhidrosis, possibly by increasing sweat gland size and sweat production.

The amino acid tyrosine serves the following three biochemical purposes. First, it is essential for the production of the thyroid products thyroxine and triiodothyronine. Second, it is essential in the production of the adrenal gland products norepinephrine (also known as "noradrenalin") and epinephrine (also known as "adrenalin"), according to the following sequence:

Tyrosine→DOPA→Dopamine→Norepinephrine

In the medullary portion of the adrenal gland, norepinephrine is converted to epinephrine, which stimulates the nervous system to produce sweat. Finally, tyrosine is critical to the production of acetylcholine, the major component of sweat gland granules.

The amount of tyrosine can be increased for additional effectiveness except that high doses of tyrosine may interfere with the estrus cycles of fertile mares. To enhance the beneficial effects of tyrosine, and to avoid interference with the estrus cycle, it is preferred to add to the twice-daily dose of approximately 500 mg of tyrosine cobalt and iodine (in the form of kelp), to facilitate synthesis of the products derived from tyrosine. Cobalt is essential in the formation of vitamin B12 and also enhances thyroid activity. Iodine is essential to the thyroid products. The preferred weight ratio of cobalt to tyrosine is in the range of about 0.0045–0.0055; the preferred weight ratio of kelp to tyrosine is in the range of about 0.00025–0.00030. Grapefruit seed extract, a preservative and natural antibiotic, and alfalfa powder, a filler which facilitates measuring the composition, can be added if desired.

The preferred composition of the first embodiment is as follows:

| Tyrosine | 1000.00 mg. |
| --- | --- |
| Cobalt | 5.00 mg. |
| Iodine (as kelp) | 0.27 mg. |
| Grapefruit seed extract | 1.33 mg. |

The above composition should be administered in ½ level teaspoon doses twice daily for a 900–1000 pound horse. The dose can be increased or decreased proportionately depending on the weight of the animal.

In a second embodiment, lecithin is added to the twice-daily dose of tyrosine in an amount sufficient to achieve a weight ratio of lecithin to tyrosine in the range of about 1.8 to 2.2. Lecithin, derived from soy protein, is an excellent source of phosphatidyl choline and phosphatidyl ethanolamine, which are both necessary precursors to acetylcholine, the major constituent of sweat gland granules. As with the first embodiment, it is preferred to add cobalt and iodine (in the form of kelp) to the tyrosine and lecithin. The weight ratio of cobalt to tyrosine should be in the range of about 0.008–0.012; the weight ratio of kelp to tyrosine should be in the range of about 0.00050–0.00060. As with the first embodiment, grapefruit seed extract and alfalfa powder can be added if desired.

The preferred composition of the second embodiment is as follows:

| Tyrosine | 500.00 mg. |
| --- | --- |
| Lecithin | 1000.00 mg. |
| Cobalt | 5.00 mg. |
| Iodine (as kelp) | 0.27 mg. |
| Grapefruit seed extract | 1.33 mg. |

The above composition should be administered in one level teaspoon doses twice daily for a 900–1000 pound horse. The dose can be increased or decreased proportionately depending on the weight of the animal.

The following examples further illustrate various features of the invention but are intended in no way to limit the scope of the invention which is defined in the appended claims.

EXAMPLE 1

The horse which was the subject of this Example resides in eastern Pennsylvania. During a humid summer the horse exhibited symptoms characteristic of anhidrosis. After three-hour rides during humid conditions, the horse exhibited a dry coat and hard blowing. The horse's respiration rate was 180 breaths per minute, and its temperature reached 107° F. The horse's anhidrotic condition was subsequently confirmed with intradermal terbutaline injections. Eight sites on the left side of the horse's neck were tested with terbutalin in doses from 1:1000 to 1:1,000,000; as a control, two sites on the right side of the horse's neck were tested with intradermal epinephrine injections. Under such tests, normal horses exhibit spidery patterns of sweat within minutes around all injection sites. In contrast to normal horses, the subject horse failed to produce sweat at any of the terbutaline sites, but produced a quarter-sized patch of sweat on the right side of its neck approximately 50 minutes after the epinephrine injections.

A dietary supplement was prepared having the following composition:

| Tyrosine | 1000.00 mg. |
| --- | --- |
| Cobalt | 5.00 mg. |
| Iodine (as kelp) | 0.27 mg. |
| Grapefruit seed extract | 1.33 mg. |

Sufficient alfalfa powder was added as a filler to bring the total volume of the composition up to ½ teaspoon. The subject horse was given ½ teaspoon of the above composition twice daily for several months, and exhibits normal equine sweating, coat and blowing patterns.

EXAMPLE 2

The horse which was the subject of this Example resides in New Jersey, a humid state. It was diagnosed anhidrotic by the procedure outlined in Example 1. A biopsy of the horse's sweat glands revealed 15% observable damage. The horse was treated with twice-daily ½ level teaspoon dosages of a supplement having the composition stated in Example 1. After two months of treatment, a biopsy of the horse's sweat glands revealed a reduction in observable damage to 8%.

EXAMPLE 3

Hypothetically, a supplement having the following composition may be prepared:

| Tyrosine | 500.00 mg. |
|---|---|
| Lecithin | 1000.00 mg. |
| Cobalt | 5.00 mg. |
| Iodine (as kelp) | 0.27 mg. |
| Grapefruit seed extract | 1.33 mg. |

The above supplement may be administered to an anhidrotic 900–1000 pound horse in twice-daily teaspoon dosages. It is predicted that the horse will experience a cessation of anhidrotic symptoms as a result of the regular administration of the supplement.

It will be readily apparent to those skilled in the art that a number of modifications and changes can be made without departing from the spirit and scope of the present invention. Therefore, it is not intended that the invention be limited by the illustrative examples but only by the claims which follow.

I claim:

1. A method for treating equine anhidrosis, the method comprising the step of administering to a horse a therapeutically effective amount of tyrosine.

2. The method of claim 1, wherein the therapeutically effective amount is a twice daily dose of at least 500 mg tyrosine per 900 pounds of weight.

3. The method of claim 2, further comprising the step of adding cobalt and kelp to the tyrosine.

4. The method of claim 3 wherein the weight ratio of cobalt to tyrosine is in the range of about 0.0045–0.0055 and the weight ratio of kelp to tyrosine is in the range of about 0.00025–0.00030.

5. The method of claim 1 further comprising the step of adding lecithin to the tyrosine.

6. The method of claim 5, wherein the weight ratio of lecithin to tyrosine is in the range of about 8–2.2.

7. The method of claim 6, further comprising the step of adding cobalt and kelp to the tyrosine and lecithin.

8. The method of claim 2, further comprising the step of adding lecithin to the tyrosine.

9. The method of claim 8, wherein the weight ratio of lecithin to tyrosine is in the range of about 8–2.2.

10. The method of claim 9, further comprising the step of adding cobalt and kelp to the tyrosine and lecithin.

11. The method of claim 10 wherein the weight ratio of cobalt to tyrosine is in the range of about 0.008–0.012 and the weight ratio of kelp to tyrosine is in the range of about 0.00050–0.00060.

12. A composition for treating equine anhidrosis comprising a therapeutically effective amount of tyrosine, cobalt and kelp.

13. The composition of claim 12 wherein the therapeutically effective amount of tyrosine is a twice daily dose of at least 500 mg tyrosine per 900 pounds of weight, the weight ratio of cobalt to tyrosine is in the range of about 0.0045–0.0055 and the weight ratio of kelp to tyrosine is in the range of about 0.00025–0.00030.

14. The composition of claim 12, further comprising lecithin.

15. The composition of claim 14, wherein the weight ratio of lecithin to tyrosine is in the range of about 1.8–2.2, the weight ratio of cobalt to tyrosine is in the range of about 0.008–0.012, and the weight ratio L of kelp to tyrosine is in the range of about 0.00050–0.00060.

16. The method of claim 2, further comprising the step of adding cobalt to the tyrosine.

17. The method of claim 16 wherein the weight ratio of cobalt to tyrosine is in the range of about 0.0045–0.0055.

* * * * *